United States Patent [19]

Cares

[11] 4,065,512

[45] Dec. 27, 1977

[54] ISO-C$_4$ COMPOUND REACTIONS WITH PERFLUOROSULFONIC ACID RESIN CATALYSTS

[75] Inventor: William R. Cares, Houston, Tex.

[73] Assignee: Petro-Tex Chemical Corporation, Houston, Tex.

[21] Appl. No.: 702,948

[22] Filed: July 6, 1976

[51] Int. Cl.$^2$ .......................... C07C 29/04; B01J 27/02
[52] U.S. Cl. .................................. 260/641; 260/682; 260/683.15 A; 252/439
[58] Field of Search .......................................... 260/641

[56] References Cited
U.S. PATENT DOCUMENTS

| 3,256,250 | 6/1966 | Frilette | 260/641 |
| 3,328,471 | 6/1967 | Kronig et al. | 260/641 |
| 3,950,442 | 4/1976 | Vogel et al. | 260/641 |
| 3,994,983 | 11/1976 | Webers et al. | 260/641 |

OTHER PUBLICATIONS

DuPont "Innovation," vol. 4, No. 3, Spring (1973).
Watsuzawa et al., "Chem Absts," vol. 82, 155310(t), 1975.

Primary Examiner—Bernard Helfin
Assistant Examiner—G. T. Breitenstein
Attorney, Agent, or Firm—Kenneth H. Johnson

[57] ABSTRACT

Perfluorosulfonic acid resin membranes are active catalysts for the hydration and polymerization of isobutene and dehydration of t-butanol. The membranes offer unique advantages for hydration and dehydration since they are semi-permeable to water and impermeable to hydrocarbons.

9 Claims, No Drawings

ISO-$C_4$ COMPOUND REACTIONS WITH PERFLUOROSULFONIC ACID RESIN CATALYSTS

BACKGROUND OF THE INVENTION

The present invention relates to the reaction of isobutene by contact with perfluorosulfonic acid resins. More particularly the present invention relates to the hydration and polymerization of isobutene or the dehydration of t-butanol employing these resins.

The acid catalysis of the reaction of isobutene and water to produce t-butanol and/or dimers, trimers, tetramers and other oligomers is well known. More recently acid ion exchange resins have been used as the catalysts, e.g., British Pat. Specification 1,390,164 and 1,396,488, where the reaction of propylene and water was illustrated in a fixed bed acidic ion exchange resin.

For t-butanol production fixed bed procedures have been proposed as the most desirable arrangement because of the simplicity of operation, i.e., water and isobutene are passed over the catalyst, the phases separated and t-butanol separated from the organic phase and/or the water phase. A rapid increase in by-product formation has characterized such operation. At the beginning of the process, the reaction proceeds as expected, with high selectivity for the production of t-butanol. Side reactions begin and increase as the reactions proceed, with a substantial reduction of t-butanol formation. The side reactions include particularly polymerization, which is uncontrolled and from which result diisobutene, triisobutene, higher oligomers, and codimers of isobutene and n-butenes.

The formation of diisobutene and triisobutene may not be particularly undesirable since these materials are of commercial interest. The higher oligomers, however, are substantially waste and in some cases are dark, gummy materials. Furthermore, the uncontrolled side reaction is a detriment, since product distribution cannot be adjusted as desired. It should also be noted in the prior art that by-product selectively could be reversed only by the secession of the reaction, back washing of the catalyst with water or replacement of the catalyst.

U.S. Pat. No. 3,328,781 issued to Kronig, et al employed a fluidized system. t-Butanol is recovered by distillation from the hydro-carbon phase and the water - resin phase is recycled to the reactor. The selectivity to t-butanol remained high.

A fluidized system is inherently less desirable because the catalyst is mixed into the reactants and some portion may remain in the hydrocarbon fraction, requiring an additional separation; and attritive action of the fluidized bed may cause disintegration of the catalysts.

The present invention employs an acid resin which may be employed as granules or particles in a prior art fixed or fluidized bed, however, the perfluorosulfonic acid resins are readily formed into stable films or membranes which have permeability properties which make them adapted to a novel method of reacting isobutene to produce t-butanol and polymers or dehydrating t-butanol to produce isobutene.

SUMMARY OF THE INVENTION

Briefly stated, the present invention is a process for catalytically reacting tertiary $C_4$ organic compounds comprising contacting isobutene; isobutene and water or t-butanol with a perfluorosulfonic acid resin and recovering a product containing isobutene polymers; t-butanol or isobutene respectively. Some isobutene polymers may also be present in the product of the hydration and dehydration reactions.

One particular aspect of the present invention is the process described comprising as the catalysts a membrane or film of perfluorosulfonic acid resin of about 2 to 20 mils thickness and preferably up to about 10 mils. The process may be carried out in gas phase or liquid phase at temperatures generally in the range of 0° to 150° C. preferably 15° to 90° C. Thus, the reactions may be carried out at atmospheric superatmospheric or subatmospheric pressures.

t-Butanol is the principal product when water is present as a reactant. Also, small quantities of isobutene polymers, i.e., dimer, trimer, tetramer, and some higher oligomers are produced as coproducts of the t-butanol. In the absence of water the polymers are the principal product. The perfluorosulfonic acid resin membranes are semi-permeable to water but impermeable to hydrocarbons. Hence, when water is a reactant, the reaction is conveniently carried out by having the membrane separating the isobutene and water reactants.

The perfluorosulfonic acid resin is present in at least an amount to catalyze the reactions, and as noted above and hereinafter it may be employed as a structural element of the reactor.

The present process is also useful for the dehydration of tertiary butanol to produce isobutene as the principal product.

In the polymerization of isobutene, it is desirable that the reaction system be substantially anhydrous.

The term "principal product" or similar language is understood to mean that the selectivity for the material so designated is greater than the selectivity (mole percent) of any other product, not withstanding the degree of conversion nor the actual percent selectivity of the product so designated.

DETAILED DESCRIPTION OF THE INVENTION AND ILLUSTRATIVE EMBODIMENTS

The perfluorosulfonic acid resins are copolymers of sulfonyl fluorovinyl ether and a fluorocarbon and may have the following formula:

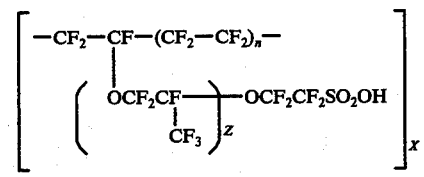

where X represents repeating units. Actually the so-called XR resin (the sulfonyl fluoride form) is produced first and made into film. Then the fluoride film is hydrolyzed to the sodium sulfonate, which is finally converted to the acid form.

The formula weight corresponding to one sulfonyl acid group is called the equivalent weight. The properties of the resin depend on the equivalent weight; the higher the equivalent weight, the higher is the mechanical strength, but also the higher is the electrical resistance. Perfluorosulfonic acid resin with useful properties has an equivalent weight ranging from 1,100 to 1,500, corresponding to Z = 1, and n = 15 to 20.

The commercial resin membrane is 5 to 10 mils thick and is sometimes laminated with a polytetrafluoroethylene web to improve mechanical strength and dimensional stability.

A further description of the perfluorosulfonic acid resin is given in DuPont "Innovation", Volume 4, No. 3, Spring, 1973.

The conversion of one surface of perfluorosulfonic acid resin films and supported film to sulfonamide/salt forms is disclosed in U.S. Pat. Nos. 3,784,399; 3,770,567 and 3,849,243, by treatment of the basic perfluorosulfonic acid resin film with ammonia gas and subsequent hydrolyzing of the other side of the film to the sodium or acid form. These modified films improved permselectivity over the free acid or Na salt form.

The reaction, i.e., hydration, dehydration or polymerization may be carried out by contacting the reactant(s) with one or both surfaces of the resin membrane. The benefit of employing the water permeable membrane in the hydration reaction of isobutene to produce t-butanol is that the hydrocarbon feed is retained on one side of the membrane and the water reactant on the other side of the membrane. Since the membrane is semi-permeable to the extent that water molecules are easily transported therethrough the reaction proceeds as if there were an actual mixture of isobutene and water. The effect is substantially the same as prior art where isobutene and an excess of water are physically mixed. The water which transported through the membrane is substantially all reacted, hence, the downstream separation of the alcoholwater mixture is eliminated. The perfluorosulfonic acid resin membrane serves in this instance as both catalyst and separation medium.

Similarly, t-butanol may be dehydrated by contacting the t-butanol with one side of the membrane while passing dry fluid, e.g., gas or liquid other than water on the other side of the membrane thereby removing the water of dehydration through the membrane. The recovered product shows a high selectivity to the isobutenes.

Since both liquid and gas phase operations are contemplated, the volume of material contacting the membrane or passing into the reactor can vary over a wide range, however, LHSV of 0.1 to 3.0 is considered an appropriate range for the isobutene (or t-butanol in the case of dehydration). Water and drying gases used in conjunction therewith as described herein are adjusted accordingly.

The principle problem one may encounter in carrying out the process, i.e., hydration, polymerization or dehydration of the present invention is in reactor design to afford reactant contract to the membrane. Poor contact will hold conversion down. Reactor design is not a part of the present invention, although several arrangements have been tried. For example, a single membrane has provided a divider in a reactor where isobutene was fed to one side and water to the other and product t-butanol removed from the isobutene side. In another configuration discs of the membrane were extended alternating from the center thermal well and side wall of a tubular reactor. Other configurations are a tube formed from the membrane, located in a concentric tube or a plurality of tubes of membrane enclosed in a chamber. The following examples will illustrate the invention as described.

HYDRATION

EXAMPLE 1

A reactor was constructed by sealing a 63.6 cm² piece of 10 mil thick Nafion Membrane 120[1] between two pyrex reaction kettle tops. The volume of the reactor, on either side of the membrane, was considerably larger than optimum and was such that a large amount of reactant isobutene gas could flow into and out of the reactor without coming into contact with the catalytic membrane surface; the use of Apiezon W sealing wax limited the reactor to temperatures below ~ 80° C. The reactor assembly was thermostated in a water bath. The investigated temperature range of 20° – 64° C. yielded energy of activation data for tert-butanol production; $E_{ACT} = 19 \pm 1$ kcal/mole. Volume tert-butanol production was investigated in the temperature range of 68° –81° C. Gas phase product analysis indicated only ~ 2.5 percent conversion of the isobutene feed with a 96 percent selectivity to tert-butanol; isobutene dimer and trimer in a 1 to 2 weight ratio were the other products obtained. Increasing the water vapor feed rate to the one side of the reactor increased the selectivity to tert-butanol on the opposite side of the reactor. Analysis of the 0° C trapped liquid product of the reaction showed 75.5 percent tert-butanol, 0.4 percent isobutene dimer and 24.2 percent isobutene trimer.

[1]"Nafion" Membrane 120 - a homogeneous film 10 mils thick of 1200 equivalent weight perfluorosulfonic acid resin. E. I. DuPont de Nemours & Co.

EXAMPLE 2

The membrane (Nafion 811 tubing[2]) was in the form of a tube approximately 1/16 inch O.D. and was contained within a second plastic tube of 1/8 inch O.D. Liquid water was passed through the inner bore of the membrane tube while isobutene gas was passed through the void space between the two tubes; the product and any remaining isobutene gas were passed to a condensing trap held at approximately 20° C., from which the excess gas was vented. The tubing reactor was heated for approximately 60 inches of its length in a water bath. The following Table I lists the approximate reaction temperature and the analysis of the liquid products.

[2]"Nafion" Tubing 811 - Tubing of 1100 equivalent weight perfluorosulfonic acid resin. Nominal 25 mils inside diameter and 35 mils outside diameter. E. I. DuPont de Nemours & Co.

Table I

| | H₂O/t-BuOH Split | | Organic Split | | |
|---|---|---|---|---|---|
| Temp. | H₂O | t-BuOH | t-BuOH | Isobutene Dimer | Isobutene Trimer |
| 20° – 40° C | 99.8%wt | 0.2%wt | 24%wt | 25%wt | 51%wt |
| 60° C | 97.5%wt | 2.5%wt | >78%wt | <10%wt | <12%wt |
| 96° C | 99.0%wt | 1.0%wt | 84%wt | 10%wt | 6%wt |

OLIGOMERIZATION

EXAMPLE 3

A reactor was constructed of Nafion Membranes 425[3] discs in a 1 inch O.D. quartz reactor tube. The discs were alternated in size and supported alternately against the reactor wall and the central thermocouple well so as to cause radial reactant flow superimposed upon the normal axial flow. The total exposed surface area of the discs was 250.0 cm². Isobutene was passed through this reactor at a rate such that all the isobutene either reacted or was retained in the 0° C trapped liquid product; analytical data on the liquid products collected is given in Table II.

[3]"Nafion" Membrane 425 - a homogenous film 5 mils thick of 1200 equivalent weight perfluorosulfonic acid resin laiminated with T-12 fabric of "Teflon TFE resin. E. I. DuPont de Nemours & Co.

Lowering the reaction temperature produces relatively larger amounts of higher molecular weight oligomers.

Table II

ISOBUTENE OLIGOMERIZATION CATALYZED BY NAFION 425

3rd Nafion Reactor (Discs) (250.0 cm² Area)

| Hours | Temp. °C. | Wt. % Dimer | Wt. % Trimer | Wt. % Tetramer | ml Prod. cm²/min. | Ratio Trimer/Dimer | Ratio Tetramer/Trimer |
|---|---|---|---|---|---|---|---|
| ~1000–1255 | 145 | 50.78 | 47.44 | 1.78 |  | 0.9342 | 0.03752 |
| 1255–1355 | 139 | 64.69 | 34.33 | 0.973 | 0.00100 | 0.5307 | 0.02835 |
| 1355–1506 | ~110 | 42.63 | 53.57 | 3.80 | 0.00079 | 1.2566 | 0.07097 |
| 1506–1546 | 100 | 34.60 | 58.53 | 6.87 | 0.00091 | 1.6917 | 0.11730 |
| 1546–0815 |  | 19.69 | 72.78 | 7.53 |  | 3.6971 | 0.1035+ |

EXAMPLE 4

The apparatus consisted of a Nafion 811 tube of ~ 1/16 inch O.D. positioned within a ⅛ inch O.D. plastic tube; approximately 60 inches of this tubing assembly was in a water bath at approximately 100° C. Isobutene gas was passed through the void space between the two concentric tubes; no water or other fluid flow occurred through the Nafion tubing 811; however, traces of water may have remained from previous experiments. The product/isobutene effluent was cooled to ~ 20° C and the so obtained liquid analyzed for its organic components. The analysis showed the following concentrations of organic materials: Feed: Isobutene Product:
tert-butanol —1% wt.
isobutene dimer—83% wt.
isobutene trimer—16% wt.

DEHYDRATION

EXAMPLE 5

Dehydration of Tert-Butanol Catalyzed by Nafion Membranes

A reactor was constructed from reaction kettle tops using RTV silicon sealant and employing a silicon oil bath for higher temperature operation. A Nafion Membrane 425 (63.6cm²) was used. tert-Butanol vapor in a helium stream was fed to one side of the reactor while a pure helium flow removed water from the opposite side of the reactor. The −78° C trapped effluent liquid from the tert-butanol feed side of the reactor had the approximate composition of 77% unreacted tert-butanol, 15% isobutene, 4% isobutene dimer, and 4% isobutene trimer. Again, non-optimum reactor design is undoubtedly responsible for the low conversions of tert-butanol.

The invention claimed is:

1. A process for producing t-butanol comprising contacting isobutene and water with a membrane of a perfluorosulfonic acid resin which is the copolymer of sulfonyl fluorovinyl ether and a fluorocarbon at a temperature in the range of about 0° to 150° C, said membrane separating said isobutene and water and recovering a product containing t-butanol.

2. The process according to claim 1 carried out in vapor phase.

3. The process according to claim 1 carried out in liquid phase.

4. The process according to claim 1 wherein the temperature is in the range of 15 to 90° C.

5. The process according to claim 1 where isobutene is contacted with one side of a membrane of perfluorosulfonic acid resin and water is contacted at the same time with the opposite side of said membrane at a temperature of 0° to 150° C and t-butanol recovered from the isobutene.

6. The process according to claim 5 wherein the process is continuous and the LHSV of the isobutene is in the range of 0.1 to 3.0.

7. In the process for the preparation of the t-butanol by reacting isobutene and water in the presence of an acid catalyst at temperatures in the range of about 120° to 150° C, wherein the improvement comprises employing as the acid catalyst a membrane of a perfluorosulfonic acid resin which is the copolymer of sulfonyl fluorovinyl ether and a fluorocarbon, contacting isobutene with one side of said membrane and water with the other side thereof, said membrane separating said isobutene and water and recovering t-butanol from said isobutene contacting said membrane.

8. The process according to claim 7 wherein said perfluorosulfonic acid resin membrane in a tube.

9. The process according to claim 7 wherein said membrane is about 2 to 20 mils thick.

* * * * *